US012601861B2

(12) United States Patent
Melakari

(10) Patent No.: US 12,601,861 B2
(45) Date of Patent: Apr. 14, 2026

(54) INDEX MATCHING BASED ON GAS TO LIQUID PHASE CHANGE

(71) Applicant: Pixieray Oy, Espoo (FI)

(72) Inventor: Klaus Melakari, Espoo (FI)

(73) Assignee: Pixieray Oy, Espoo (FI)

( * ) Notice: Subject to any disclaimer, the term of this patent is extended or adjusted under 35 U.S.C. 154(b) by 744 days.

(21) Appl. No.: 18/146,482

(22) Filed: Dec. 27, 2022

(65) Prior Publication Data

US 2024/0206720 A1 Jun. 27, 2024

(51) Int. Cl.
| | |
|---|---|
| *G02B 3/14* | (2006.01) |
| *A61B 3/00* | (2006.01) |
| *A61B 3/113* | (2006.01) |
| *G02B 3/08* | (2006.01) |
| *G02B 26/00* | (2006.01) |

(52) U.S. Cl.
CPC .............. *G02B 3/14* (2013.01); *A61B 3/0025* (2013.01); *A61B 3/113* (2013.01); *G02B 3/08* (2013.01); *G02B 26/004* (2013.01)

(58) Field of Classification Search
CPC ......... A61B 3/0025; A61B 3/113; G02B 3/08; G02B 3/14; G02B 26/004; G02B 27/0093; G02B 27/0172; G02B 26/005; G02B 3/12; G02B 27/646; G02B 21/33; G02B 5/06; G02C 11/10; G02C 2202/16; G02C 2202/20; G02C 7/083; G02C 7/085; F04F 7/00
See application file for complete search history.

(56) References Cited

U.S. PATENT DOCUMENTS

| | | | | |
|---|---|---|---|---|
| 4,890,914 | A | * | 1/1990 | Templeton ........... G01B 11/162 |
| | | | | 359/666 |
| 6,867,923 | B2 | * | 3/2005 | Singer .................. G02B 13/143 |
| | | | | 359/667 |
| 2007/0188882 | A1 | * | 8/2007 | Cernasov ............. G02B 3/0056 |
| | | | | 359/659 |
| 2008/0106711 | A1 | * | 5/2008 | Beierl ................ G03F 7/70891 |
| | | | | 355/30 |
| 2014/0002790 | A1 | * | 1/2014 | Pugh ...................... G02C 7/085 |
| | | | | 351/159.39 |

FOREIGN PATENT DOCUMENTS

| | | | | | |
|---|---|---|---|---|---|
| CN | 108549139 | A | * | 9/2018 | ............. G02B 7/182 |
| CN | 113791467 | A | * | 12/2021 | ............... G03B 3/04 |
| WO | WO-2018076153 | A1 | * | 5/2018 | ............... G02B 3/14 |

* cited by examiner

*Primary Examiner* — Matthew Y Lee
(74) *Attorney, Agent, or Firm* — Ziegler IP Law Group, LLC.

(57) ABSTRACT
Disclosed is an optical element with a first substrate and a second substrate. A cavity is formed between first substrate and second substrate; a material, wherein liquid state of material has refractive index that matches refractive index of at least one of: first substrate, second substrate; a liquid reservoir that is to be employed to hold liquid state; a gas reservoir that is to be employed to hold a gaseous state of the material; means for converting gaseous state into liquid state; fluid channel(s) connecting cavity to liquid reservoir and to gas reservoir; and means for controlling supply of liquid state to cavity through fluid channel(s) and for controlling replacement of liquid state with the gaseous state in cavity, wherein given optical power is produced by optical element when cavity is filled with gaseous state.

14 Claims, 3 Drawing Sheets

200

202a 204a 202b 204b 202c

300

INDEX MATCHING BASED ON GAS TO LIQUID PHASE CHANGE

TECHNICAL FIELD

The present disclosure relates to optical elements incorporating index matching. The present disclosure also relates to optical apparatuses comprising such optical elements.

BACKGROUND

Age-related vision degradation is common in humans. As a person ages, a biological lens of her/his eye gradually loses some of its flexibility, which results in a gradual decline in an auto-focusing ability of the eye. Therefore, blurred vision and difficulty in focusing on objects at different distances are common issues related to vision degradation. Using powered eyeglasses for vision correction is therefore common.

When vision is to be corrected both for distance viewing and reading, eyeglasses implementing multifocal lenses (for example, such as bifocal, trifocal and progressive lenses) are commonly used. Such multifocal lenses incorporate two different prescriptions (namely, for distance viewing and reading) in a single lens. However, users often find it difficult to accommodate with such multifocal lenses. This is primarily because such a multifocal lens has multiple optical centres, and an area between these optical centres is prone to distortion, peripheral aberrations, and prismatic artefacts. Moreover, manufacturing such lenses is usually difficult and expensive.

In an attempt to overcome this problem, some conventional optical apparatuses use a spatial light modulator (SLM), which employs a liquid crystal material to spatially vary a modulation of a beam of light, thereby changing a diffraction pattern of the beam of light. However, SLMs suffer from several disadvantage. Firstly, a large SLM requires a complex driving circuit that needs complex electronics, and hence makes it difficult to achieve requirements of low power consumption and good integration level. Secondly, SLMs are used to make diffractive lenses, which are known to suffer from poor sharpness, poor colour performance, poor transparency, and a narrow field of view.

Some other conventional optical apparatuses use lenses that changes a shape of an optical surface. Examples of such lenses include, but are not limited to, liquid lens, and semi-rigid polymer lenses. However, such lenses are slow in operation, are bulky, and degrade over time. Yet other conventional optical apparatuses use lenses that utilizes gradient index modulation. Hence, such lenses have flat surfaces due to a gradual variation in a refractive index of a material used for manufacturing these lenses. Examples of such lenses include, but are not limited to, liquid crystal lenses, and micro crystalline cellulose lenses. However, such lenses are prone to distortion and visual artefacts in extreme temperatures. Still other conventional optical apparatuses use switchable lenses, which can be turned on or off as per user's need. Typically, this is done by immersing a lens into a structure that has a same refractive index as the lens itself. Hence, due to no refractive index difference, an optical power of the lens disappears. The refractive index difference can be re-introduced to generate the optical power by employing methodologies, for example, such as, electro vetting, mechanical movement, wetting, or similar. However, such methodologies are expensive and time-intensive.

Therefore, in light of the foregoing discussion, there exists a need to overcome the aforementioned challenges associated with conventional optical elements and optical apparatuses employing such optical elements.

SUMMARY

The present disclosure seeks to provide an improved optical element. The present disclosure also seeks to provide an optical apparatus comprising such an optical element. An aim of the present disclosure is to provide a solution that overcomes at least partially the problems encountered in prior art.

In a first aspect, an embodiment of the present disclosure provides an optical element comprising:

a first substrate and a second substrate that are optically transparent, wherein a cavity is formed between the first substrate and the second substrate;

a material that is optically transparent, wherein a liquid state of the material has a refractive index that matches a refractive index of at least one of: the first substrate, the second substrate;

a liquid reservoir that is to be employed to hold the liquid state of the material;

a gas reservoir that is to be employed to hold a gaseous state of the material;

means for converting the gaseous state of the material into the liquid state of the material, said means for converting being connected to the gas reservoir and to the liquid reservoir;

at least one fluid channel connecting the cavity to the liquid reservoir and to the gas reservoir; and means for controlling a supply of the liquid state of the material to the cavity through the at least one fluid channel and for controlling a replacement of the liquid state of the material with the gaseous state of the material in the cavity, wherein a given optical power is produced by the optical element when the cavity is filled with the gaseous state of the material.

In a second aspect, an embodiment of the present disclosure provides an optical apparatus comprising at least one optical element of the first aspect.

Embodiments of the present disclosure substantially eliminate or at least partially address the aforementioned problems in the prior art, and provides a simple, accurate, less power-intensive production of the given optical power by way of index matching based on gas to liquid phase change, in real time or near-real time.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
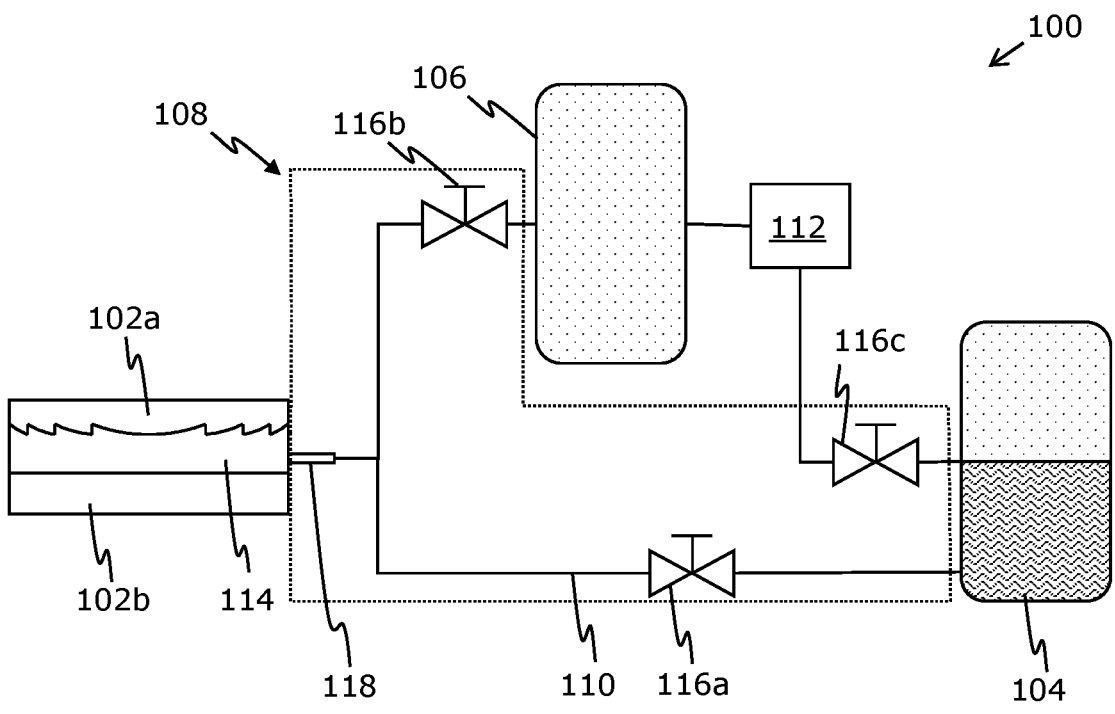
FIGS. 1A, 1B, and 1C illustrate schematic diagrams of an optical element, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, an embodiment of the present disclosure provides an optical element comprising:

a first substrate and a second substrate that are optically transparent, wherein a cavity is formed between the first substrate and the second substrate;

a material that is optically transparent, wherein a liquid state of the material has a refractive index that matches a refractive index of at least one of: the first substrate, the second substrate;

a liquid reservoir that is to be employed to hold the liquid state of the material;

a gas reservoir that is to be employed to hold a gaseous state of the material;

means for converting the gaseous state of the material into the liquid state of the material, said means for converting being connected to the gas reservoir and to the liquid reservoir;

at least one fluid channel connecting the cavity to the liquid reservoir and to the gas reservoir; and means for controlling a supply of the liquid state of the material to the cavity through the at least one fluid channel and for controlling a replacement of the liquid state of the material with the gaseous state of the material in the cavity, wherein a given optical power is produced by the optical element when the cavity is filled with the gaseous state of the material.

In a second aspect, an embodiment of the present disclosure provides an optical apparatus comprising at least one optical element of the first aspect.

The present disclosure provides the aforementioned optical element and the aforementioned optical apparatus. Pursuant to embodiments, the optical element produces different optical powers by changing a state of the material filled in the cavity that is formed between the first substrate and the second substrate. Such an optical element is easy to manufacture, as it does not require any advanced manufacturing processes, for example, as compared to conventional liquid crystal lenses. Notably, the optical element does not require any electrically conductive layers to adjust the optical power. The optical element requires relatively simple driving electronics. Moreover, the cavity can be made bigger. Owing to such simple manufacturing requirements, the optical element could be made at low cost in high volumes. Furthermore, a transparency of the optical element is significantly better than conventional liquid crystal lenses; liquid crystal materials are known to be somewhat light absorbing and light scattering. Moreover, the aforesaid optical element can be operated to produce the given optical power with a fast response time. This facilitates the user to experience high visual acuity and minimum haze level when looking in a real-world environment. Furthermore, the material filled between the cavity is able to produce the given optical power even in extreme temperatures. The optical element is simple, light-weight, robust, reliable, and can be implemented with ease. The aforementioned optical apparatus is optically efficient, while having low power requirements.

Throughout the present disclosure, the term "optical element" refers to an active optical element whose optical power can be changed. In other words, the optical power of the optical element is adjustable. In this regard, the optical element is (optionally electrically) controlled to produce the given optical power.

A refractive index of the first substrate can be same as or different from a refractive index of the second substrate. Moreover, the first substrate and/or the second substrate can be made of any one of: a glass, a polycarbonate, a plastic, a high-index plastic. A person skilled in the art will recognize many variations, alternatives, and modifications of embodiments of the present disclosure.

The material could be in the liquid state or in the gaseous state inside the cavity. Hence, the gaseous state of the material and the liquid state of the material are required to have optical properties, which are suitable for producing different optical powers. Examples of the material may include, but are not limited to, water, alcohol, propane, butane, and freon.

The first substrate and the second substrate are arranged in an overlapping manner, thereby forming the cavity between the first substrate and the second substrate. Optionally, the given optical power to be produced depends on a curvature of a surface of the at least one of: the first substrate, the second substrate whose refractive index matches with the refractive index of the liquid state of the material. In other words, the at least one of: the first substrate, the second substrate has a curved surface that is in contact with the material.

Throughout the present disclosure, the term "given optical power" refers to any of: the positive power, the negative power, for viewing nearby objects or for distance viewing. Thus, the curvature of the surface of the aforesaid substrate depends on user's requirements. The given optical power may be prescribed for the user's eye, or may be selected to conform with the user's need. In an example, the given optical power may need to be produced for a user suffering from presbyopia. In another example, the given optical power may need to be produced for a user suffering from both presbyopia and myopia; in such a case, apart from a positive optical power that the user may need to read or look at nearby objects, a negative optical power may be required to be produced to enable the user to see faraway objects. In this regard, the given optical power (produced by the interface of the gaseous state of the material and the aforesaid substrate) is the positive optical power. Optionally, in such a case, the negative optical power is produced as a fixed optical power by any one of: the first substrate, the second substrate that is implemented as a passive optical element.

Notably, the given optical power is produced by creating a relative refractive index between the material (that is filled in the cavity) and the aforesaid substrate. When the cavity is filled with the liquid state of the material, an interface between the material and said substrate disappears, because the refractive index of the liquid state of the material matches with the refractive index of said substrate; as a result, the optical element does not produce any optical power. On the other hand, when the cavity is filled with the gaseous state of the material, the interface between the material and said substrate re-appears, because the refractive index of the gaseous state of the material does not match with the refractive index of said substrate; as a result, the optical element produces the given optical power.

In other words, when the cavity is filled with the gaseous state of the material, a relative refractive index is generated between the gaseous state of the material and said substrate, thereby producing the given optical power. As a result, a light ray converges or diverges at the curved surface (namely, an interface between the material and the at least one of: the first substrate, the second substrate), depending on the curvature of the surface. It will be appreciated that in a case where only one of the first substrate and the second substrate has a curved surface, another one of the first substrate and the second substrate can be made significantly thin, so as to avoid unwanted convergence or divergence of the light ray.

The curved surface could be a convex surface or a concave surface, depending on whether a positive optical power or a negative optical power is to be produced. In such a case, the aforesaid substrate could be implemented as any one of: a planoconvex lens whose convex surface faces the material, a planoconcave lens whose concave surface faces the material.

Alternatively, optionally, the at least one of: the first substrate, the second substrate whose refractive index matches with the refractive index of the liquid state of the material is implemented as a Fresnel lens having concentric grooves, wherein the concentric grooves face the material. The at least one of: the first substrate, the second substrate that is implemented as the Fresnel lens is hereinafter referred to as the "Fresnel substrate", for the sake of convenience only. A shape of the concentric grooves can be refractive or diffractive. In a case where a positive optical power is to be produced, the concentric grooves of the Fresnel substrate can be formed to emulate characteristics of a planoconvex lens whose curvature corresponds to the positive optical power. In another case where a negative optical power is to be produced, the concentric grooves of the Fresnel substrate can be formed to emulate characteristics of a planoconcave lens whose curvature corresponds to the negative optical power.

A technical benefit of employing the Fresnel substrate is that it allows the optical element to operate with a thin layer of the material, i.e., an amount of the material that is required to be filled inside the cavity for generating the given optical power would be considerably less. This may also facilitate in reducing an overall weight of the optical element.

It will be appreciated that matching the refractive index of the liquid state of the material with the Fresnel substrate is a minimum requirement. However, as the thickness of the cavity varies due to the grooves of the Fresnel substrate, it is beneficial to match the refractive index of the liquid state of the material with the other substrate as well. This ensures that no optical power is produced unintentionally when the liquid state of the material is filled inside the cavity.

Moreover, the liquid reservoir holds the liquid state of the material at a given temperature and a given pressure that lie within a predefined temperature range and a predefined pressure range, respectively. The liquid reservoir could be at least partially filled with the liquid state of the material, i.e., the liquid state of the material need not be filled up to a brim of the liquid reservoir. Similarly, the gas reservoir holds the gaseous state of the material at another given temperature and another given pressure that lie within another predefined temperature range and another predefined pressure range, respectively. The predefined temperature range, the predefined pressure range, the another predefined temperature range and the another predefined temperature range depend on the material being used in the optical element. It will be appreciated that the gas reservoir could be implemented as the cavity of the optical element itself.

The means for converting is employed to convert the gaseous state of the material into the liquid state of the material, and vice-versa. For this purpose, the means for converting changes (i.e., increase or decrease) a temperature and/or a pressure of the material. The means for converting can be a mechanical device, an electrical device, an electromechanical device, or similar.

Optionally, said means for converting is implemented as a condenser and/or a compressor. Herein, the term "condenser" refers to a heat exchanger that is used to condense the gaseous state of the material into the liquid state of the material by condensation phenomenon. In other words, when a temperature of the gaseous state of the material in the gas reservoir is reduced using the condenser, the gaseous state of the material condenses and converts into the liquid state of the material. It will be appreciated that the condenser could be designed using at least one solid state device (such as a transistor, a semiconductor-based device, and the like), and may operate on the principle of Peltier effect. Optionally, said means for converting further comprises a temperature sensor for sensing a temperature of the gaseous state of the material, when the condenser is being employed for converting the gaseous state of the material to the liquid state of the material. Furthermore, the term "compressor" refers to a mechanical device which increases a pressure of the gaseous a given state of the material, by reducing a volume of the given state of the material. In an instance, the compressor may function based on a mechanical principle, or a molecular pump principle. In another instance, the compressor may function by harvesting direct body movement. As an example, a kinetic energy of a pendulum can be harvested to compress the gaseous state of the material, and thereby subsequently converting it to the liquid state of the material. Both the condenser and the compressor are well-known in the art, and can be easily used in conjunction.

Moreover, the at least one fluid channel forms a closed conduit to allow the flow of the liquid state and the gaseous state of the material through the at least one fluid channel. Such a flow would be similar to, for example, a flow of a fluid through a pipe or a tube. The at least one fluid channel allows the flow of the liquid state of the material from the liquid reservoir to the cavity, and vice-versa. Similarly, the at least one fluid channel allows the flow of the gaseous state of the material from the gas reservoir to the cavity, and vice-versa. The at least one fluid channel could be made up of a non-corrosive and a high strength material. Examples of such a material could be polyvinyl chloride (PVC), stainless steel, High-Density Polyethylene (HDP), and the like.

The flow of the gaseous state of the material and/or the flow of the liquid state of the material is controlled and/or maintained by the means for controlling. The means for controlling can be implemented to at least one of:

regulate the aforesaid flow to restrict an amount of fluid flowing through the at least one fluid channel, control a fluidic pressure of the fluid when flowing through the at least one fluid channel, maintain a direction of the aforesaid flow, for example, through valves (as discussed later), prevents backflow or leakage, of the liquid state of the material from the cavity.

Optionally, said means for controlling comprises:

a first valve arranged on the at least one fluid channel between the liquid reservoir and the cavity; and a second valve arranged on the at least one fluid channel between the gas reservoir and the cavity.

In this regard, a given valve (namely, the first valve and the second valve) is used to regulate and control a flow of a given state (namely, the gaseous state and the liquid state) of the material, to/from the cavity to a given reservoir (namely, the gas reservoir and the liquid reservoir, respectively). The given valve may be a mechanical valve, which could be controlled by an actuator. The actuator may, for example, be implemented as an electromagnetic actuator, a piezoelectric actuator, a memory metal actuator, an electro-active polymer, an electrophoresis actuator, or similar. Examples of the given valve may include, but are not limited to, a bi-directional valve, a flow control valve, a flow regulator, a flow conditioner. Optionally, the given valve is implemented as the bi-directional valve for maintaining a bi-directional flow of the given state of the material to its respective reservoir. This enables to control a flow of the given state of the material in both directions. Additionally, or alternatively, optionally, the given valve is implemented as the flow control valve for obtaining a uniform flow rate of the given state of the material through the at least one fluid channel. The flow rate of the given state of the material can be expressed in a volume of the material per unit time, such as cubic meters per second, litres per minute, or similar. Yet additionally, or alternatively, optionally, the given valve is implemented as the flow conditioner for improving a flow profile of the given state of the material in the at least one fluid channel. The flow conditioner changes a turbulent flow profile of the material to a laminar flow profile of the material. The term "given valve" encompasses at least the first valve and the second valve.

Optionally, said means for controlling further comprises a third valve arranged between the means for converting and the liquid reservoir, wherein the third valve is to be employed to control a condensation and/or a compression of the gaseous state of the material into the liquid state the material. The third valve works in a manner similar to the first valve and the second valve. An amount of liquid state of the material leaving as well as entering the liquid reservoir is regulated and controlled by the third valve.

Optionally, said means of controlling comprises a plurality of capillaries that are to be employed to control the supply of the liquid state of the material to the cavity. In this regard, the plurality of capillaries use capillary action to supply the liquid state of the material from the liquid reservoir to the cavity. Using the capillary action for transporting a fluid is well-known in the art. It will be appreciated that the plurality of capillaries are arranged in proximity of the cavity of the optical element as fine channels or tubes with very narrow diameters. It will also be appreciated that the supply of the gaseous state of the material to the cavity may be due to diffusion.

Optionally, the liquid state of the material is supplied from the liquid reservoir to the cavity by:

opening the first valve arranged between the liquid reservoir and the cavity, whilst closing the second valve arranged between the gas reservoir and the cavity; and increasing a pressure at the liquid reservoir.

In this regard, after the first valve is opened, the pressure at the liquid reservoir is increased to allow a flow of the liquid state of the material from the liquid reservoir to the cavity. Simultaneously, the second valve is closed in order to prevent a flow of the liquid state of the material into the gas reservoir. By increasing the pressure at the liquid reservoir, the liquid state of the material flows through the plurality of capillaries into the cavity. When the cavity is completely filled with the liquid state of the material, the interface between the material and the at least one of: the first substrate, the second substrate disappears. This means that the optical element is in a switched-off state, i.e., it does not produce any optical power. In order to keep the optical element in the switched-off state, the first valve can also be closed (upon filling the cavity with the liquid state of the material) to maintain the amount of the liquid state of the material inside the cavity. Both the first valve and the second valve can be kept closed until the optical element needs to be switched "on".

Optionally, the liquid state of the material is replaced with the gaseous state of the material in the cavity by:

closing the first valve arranged between the liquid reservoir and the cavity, whilst opening the second valve arranged between the gas reservoir and the cavity; and reducing a pressure of the gas reservoir.

In this regard, when the first valve is closed and the second valve is opened, the liquid state of the material (that is already present inside the cavity) is replaced with the gaseous state of the material upon reducing the pressure of the gas reservoir. When the pressure of the gas at the gas reservoir is reduced, the liquid state of the material evaporates rapidly to convert to the gaseous state of the material, thereby filling the gas reservoir with the gaseous state of the material via the at least one fluid channel. The pressure of the gaseous state of the material at the gas reservoir can be monitored by using a pressure sensor. Some amount of the gaseous state of the material is left in the cavity, while a remaining amount of the gaseous state of the material is converted to the liquid state of the material using the means for converting, and sent to the liquid reservoir by opening the third valve. It will be appreciated that when some amount of the gaseous state of the material is left in the cavity, the interface between the material and the at least one of: the first substrate, the second substrate re-appears, thereby producing the given optical power. This means that the optical element is now in a switched-on state. Both the first valve and the second valve can be kept closed, until the optical element needs to be switched "off".

Furthermore, optionally, the optical element further comprises:

at least one other substrate, wherein at least one other cavity is formed between the second substrate and the at least one other substrate, and wherein the refractive index of the liquid state of the material matches a refractive index of at least one of: the second substrate, the at least one other substrate; and at least one other fluid channel connecting the at least one other cavity to the liquid reservoir and to the gas reservoir, wherein said means for controlling is to be employed to control a supply of the liquid state of the material to the at least one other cavity through the at least one other fluid channel and to control a replacement of the liquid state of the material with the gaseous state of the material in the at least one other cavity, further wherein the given optical power is produced by the optical element when at least one of: the cavity, the at least one other cavity is filled with the gaseous state of the material.

The technical benefit of having the at least one other substrate and the at least one other cavity is that it allows for producing different optical powers. Moreover, when employing the at least one other substrate and the at least one other cavity, a separate layer of the gaseous state of the material between pairs of adjacent substrates (namely, the second substrate and the at least one other substrate) enables the optical power of the optical element to be changed in steps.

A curvature of a surface of the at least one of: the second substrate, the at least one other substrate (whose refractive index matches with the refractive index of the liquid state of the material) can be same as or different from the curvature of the surface of the at least one of: the first substrate, the second substrate. It will be appreciated that different optical powers can be generated using a same configuration of the optical element comprising the first substrate, the second substrate, and the at least one other substrate. In such a case, the given optical power produced by the optical element is a combination of respective optical powers produced when at least one of: the cavity, the at least one other cavity, is filled with the gaseous state of the material.

In an example, the second substrate could be implemented as a planoconvex lens whose convex surface faces the material encased between the first substrate and the second substrate, and whose curvature corresponds to a first positive optical power, while the at least one other substrate could be implemented as at least one other planoconvex lens whose convex surface faces the material encased between the second substrate and the at least one other substrate, and whose curvature corresponds to a second positive optical power. In another example, both the second substrate and the at least one other substrate could be implemented as Fresnel lenses having concentric grooves, wherein their concentric grooves face the material and emulate characteristics of respective ones of the planoconvex lens and the at least one other planoconvex lens. In these examples, if the first positive optical power and the second positive optical power are 1.5 dioptres and 0.75 dioptre, respectively, the given optical power can be changed in steps of 0 dioptre, 0.75 dioptre, 1.5 dioptres and 2.25 dioptres.

In an alternative example, the second substrate and the at least one other substrate could be implemented as a planoconvex lens (whose convex surface faces the material encased between the first substrate and the second substrate) and a planoconcave lens (whose concave surface faces the material encased between the second substrate and the at least one other substrate), respectively, having a positive optical power and a negative optical power. In another alternative example, both the second substrate and the at least one other substrate could be implemented as Fresnel lenses having concentric grooves, wherein their concentric grooves face the material and emulate characteristics of the planoconvex lens and the planoconcave lens, respectively. In these alternative examples, the given optical power can be the positive optical power or the negative optical power, depending on whether a user (who is suffering from both presbyopia and myopia) needs to see nearby objects or faraway objects.

Moreover, it will be appreciated that the at least one other fluid channel works in a manner similar to the at least one fluid channel. A configuration of the at least one other fluid channel can be same as or different from a configuration of the at least one fluid channel. Herein, the means for controlling works in a manner similar to the manner as described above. The liquid state of the material is supplied to the at least one other cavity by the means for controlling in a manner that is similar to the supply of the liquid state of the material to the cavity. A technical benefit of controlling the flow in such a manner is that a range of optical powers as per user's needs can be produced by controlling the flow of the liquid state of the material into the at least one of: the cavity, the at least one other cavity.

The present disclosure also relates to the optical apparatus of the second aspect. Various embodiments and variants disclosed above, with respect to the aforementioned first aspect, apply mutatis mutandis to the optical apparatus.

Throughout the present disclosure, the term "optical apparatus" refers to an apparatus that is to be worn over eyes of the user. Examples of such an optical apparatus include, but are not limited to, a pair of glasses, a pair of sunglasses, smart glasses, and a head-mounted display.

Optionally, the optical apparatus further comprises:

a frame employed to hold the at least one optical element; and at least one input means, mounted on a temple of the frame, that is to be used by a user to switch on or switch off the at least one optical element.

In this regard, the frame is designed in a manner that the at least one optical element is firmly arranged on the frame. In an example, when the optical apparatus is implemented as a pair of eyeglasses, the frame may hold two optical elements, wherein a first optical element is employed for a first eye of the user, and a second optical element is employed for the second eye of the user. It will be appreciated that a material of the frame could be plastic, metal, polymer, and the like.

The at least one input means could be implemented as one of: a physical slider, a button. The at least one input means provides a flexibility to the user using the optical apparatus by allowing the user to conveniently switch on or switch off the at least one optical element, as and when required. This may, for example, be beneficial in a scenario where the user may require a positive optical power only for a shorter duration of time during a typical day, such as when she/he wants to read or focus on nearby objects. Furthermore, in this way, power resources of the optical apparatus could also be saved.

Optionally, the optical apparatus further comprises a processor and a wireless communication interface that is to be employed to communicably couple the processor of the optical apparatus to a computing device, wherein the computing device is to be used by a user for at least one of:

switching on or switching off the at least one optical element, inputting the given optical power to be produced.

Examples of the wireless communication interface may include, but are not limited to, Internet and Bluetooth®. Examples of the computing device include, but are not limited to, a cell phone, a laptop computer, a desktop computer, a tablet computer, a phablet, a personal digital assistance. Optionally, an interactive user interface is provided on the computing device, to enable the user to perform at least one of the aforesaid operations on the computing device. It will also be appreciated that prior to inputting the given optical power to be produced, the at least one optical element could be in a pre-set mode, wherein a fixed optical power is already set for the at least one optical element. Using the computing device, such an optical power could be easily adjusted by the user, as and when required.

Optionally, the optical apparatus further comprises eye-tracking means and a processor configured to:

process eye-tracking data, collected by the eye-tracking means, to determine gaze directions of a user's eyes;

determine a given optical depth at which the user is gazing, based on at least one of: the gaze directions of the user's eyes, depth information of a real-world scene currently being seen by the user;

determine an optical power prescribed for a given eye of the user corresponding to the given optical depth at which the user is gazing, the optical element being worn in front of the given eye of the user; and determine the given optical power to be produced, based on the optical power prescribed for the given eye of the user.

Throughout the present disclosure, the term "eye-tracking means" refers to specialized equipment that is employed to detect and/or follow a direction of gaze of the user of the optical apparatus. Such eye tracking is performed when the optical apparatus, in operation, is worn by the user over his/her eyes. Optionally, the eye-tracking means is implemented by way of contact lenses having sensors, cameras monitoring features of the user's eye, and the like. Such features may comprise at least one of: a shape of a pupil of the user's eyes, a size of the pupil, corneal reflections of at least one light source from a surface of the user's eye, a relative position of the pupil with respect to the corneal reflections, a relative position of the pupil with respect to the corneal reflections, a relative position of the pupil with respect to corners of the user's eye. Such eye tracking means are well-known in the art. The term "gaze direction" refers to a direction in which a given eye of the user is gazing.

Optionally, in this case, the optical power of the optical element is automatically adjusted to the given optical power depending on a viewing distance between a user and a region at which the user is gazing. This enables the user to see objects (whether nearby or faraway) clearly at all times. The technical benefit of such a gaze-based selection is that the optical power can be adjusted at the optical element in real time or near-real time according to the user's gaze. As an example, the user may be installing a lighting fixture on a ceiling of a room, while her/his tools may be lying on a floor of the room. In such a case, the user may need to look at the lighting fixture and at the tools at different points in time, via the optical element, when the optical apparatus is worn by the user. The optical power of the optical element is appropriately adjusted to produce the given optical power when the user needs to focus on the lighting fixture (namely, a nearby object) and the tools (namely, faraway objects).

Optionally, the optical apparatus further comprises a power source to supply electrical power to the processor as well as to the means for controlling and the means for converting of the at least one optical element. Optionally, the power source can be recharged by harvesting the direct body movement. The power source and the processor may be installed at any suitable location on the optical apparatus. As an example, when the optical apparatus is implemented as a pair of glasses, the power source and the processor may be installed at a frame of said pair of glasses. The power source and/or the processor can be located at a bridge or an end of the temple of the frame.

DETAILED DESCRIPTION OF THE DRAWINGS

Figure 1B:
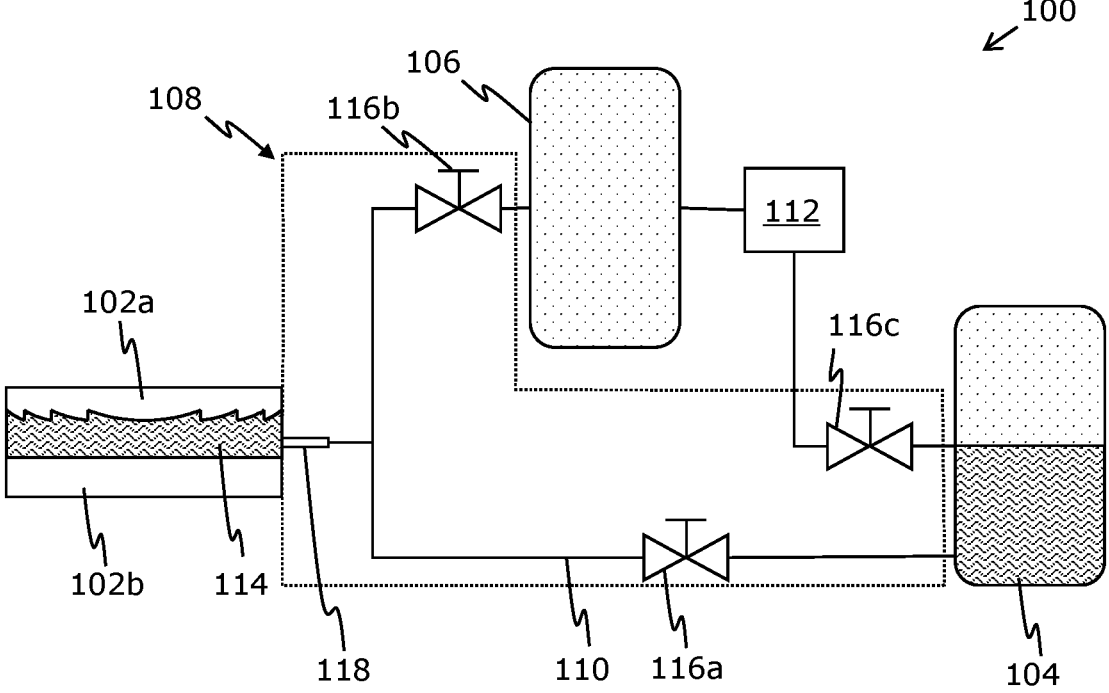
Figure 1C:
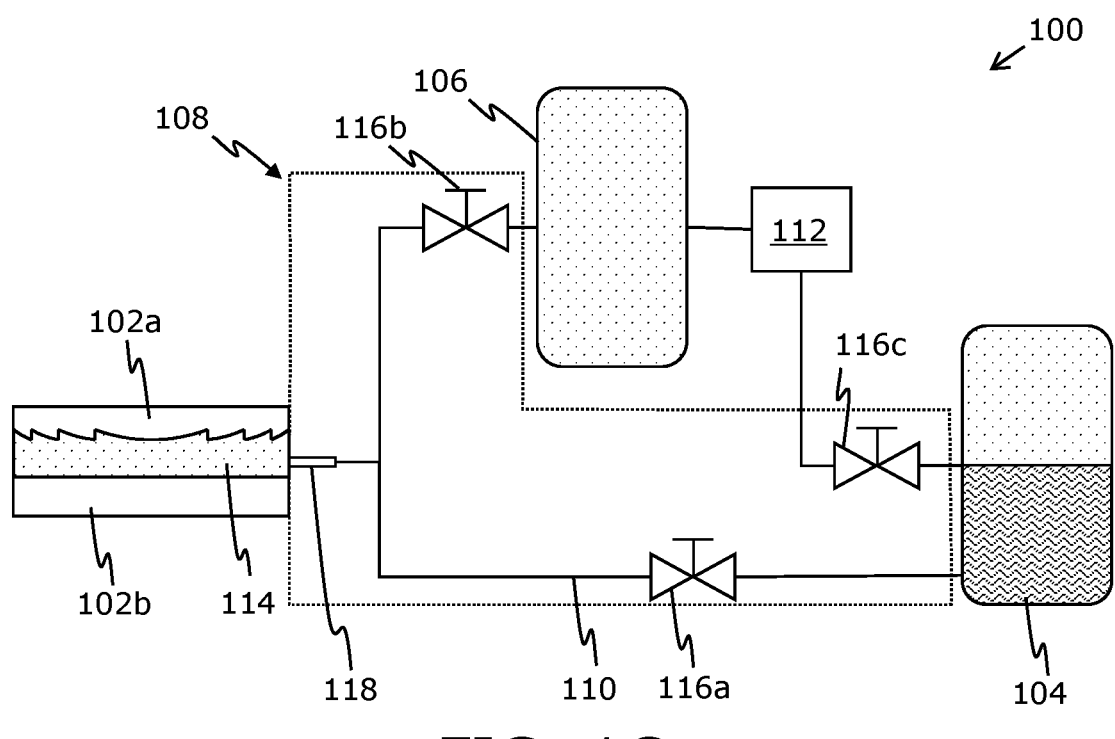

Referring to FIGS. 1A, 1B, and 1C, illustrated are schematic diagrams of an optical element 100, in accordance with an embodiment of the present disclosure. The optical element 100 comprises a first substrate 102a, a second substrate 102b, a material, a liquid reservoir 104, a gas reservoir 106, a means 108 (as depicted by a dotted line) for controlling, at least one fluid channel (as depicted by a fluid channel 110), and a means 112 for converting. A cavity 114 is formed between the first substrate 102a and the second substrate 102b. The liquid reservoir 104 is employed to hold a liquid state (as depicted using a zig zag pattern) of the material. The gas reservoir 106 is employed to hold a gaseous state (as depicted using a dotted pattern) of the material. The means 112 for converting is connected to the gas reservoir 106 and to the liquid reservoir 104. The fluid channel 110 connects the cavity 114 to the liquid reservoir 104 and the gas reservoir 106. With reference to FIG. 1A, the cavity 114 is shown empty.

Optionally, the means 108 for controlling comprises a first valve 116a and a second valve 116b. The means 108 for controlling further comprises a third valve 116c and a plurality of capillaries 118. The first valve 116a is arranged on the fluid channel 110 between the liquid reservoir 104 and the cavity 114. The second valve 116b is arranged on the fluid channel 110 between the gas reservoir 106 and the cavity 114. The third valve 116c is arranged between the means 112 for converting and the liquid reservoir 104. The plurality of capillaries 118 are arranged in close proximity to the cavity 114.

With reference to FIG. 1B as shown, the cavity 114 is filled with the liquid state of the material, wherein the refractive index of the first substrate 102a (and optionally the second substrate 102b) matches with the refractive index of the liquid state of the material, thereby producing no optical power. Optionally, the liquid state of the material is supplied from the liquid reservoir 104 to the cavity 114 by opening the first valve 116a whilst closing the second valve 116b, and increasing a pressure at the liquid reservoir 104.

With reference to FIG. 1C, the cavity 114 is filled with the gaseous state of the material, to produce a given optical power. Optionally, the liquid state of the material is replaced with the gaseous state of the material in the cavity 114 by closing the first valve 116a whilst opening the second valve 116b, and reducing a pressure at the gas reservoir 106.

FIGS. 1A, 1B and 1C are merely examples, which should not unduly limit the scope of the claims herein. It is to be understood that the specific implementations of the optical element 100 are provided as examples and are not to be construed as limiting it to specific types and numbers of substrates, liquid reservoirs, gas reservoirs, means for converting, means for controlling, fluid channels, cavities, valves, or capillaries. A person skilled in the art will recognize many variations, alternatives, and modifications of embodiments of the present disclosure.

Figures 2A, 2B:
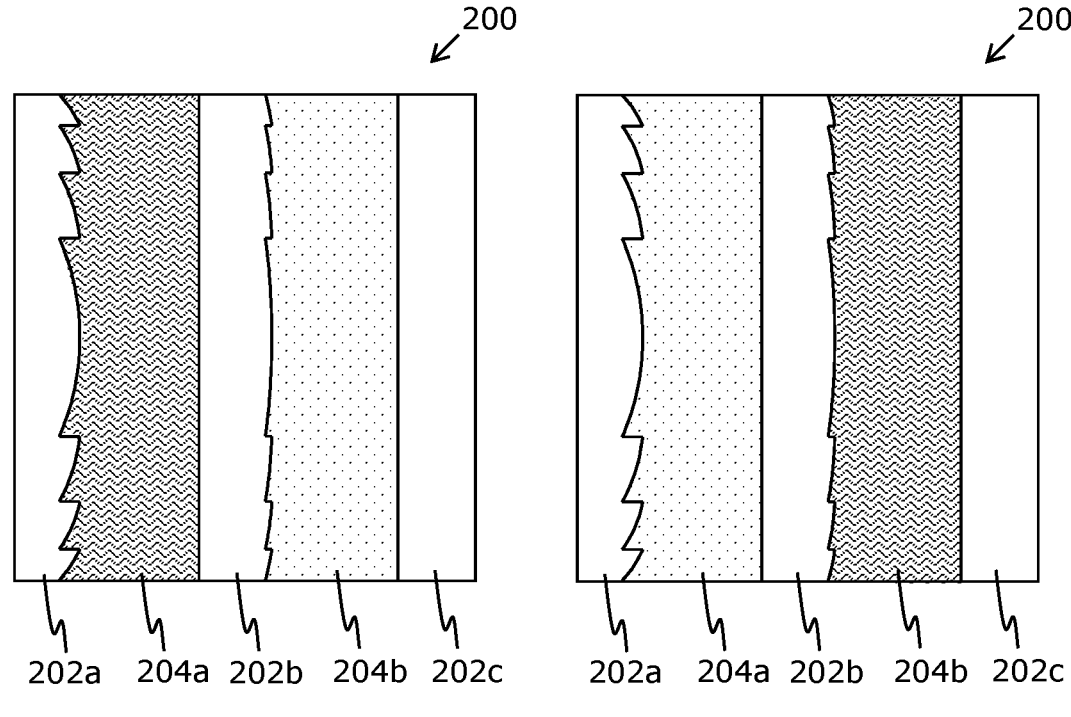
FIGS. 2A, 2B, and 2C illustrate example ways in which an optical element can produce different optical powers, in accordance with an embodiment of the present disclosure.
Figure 2C:
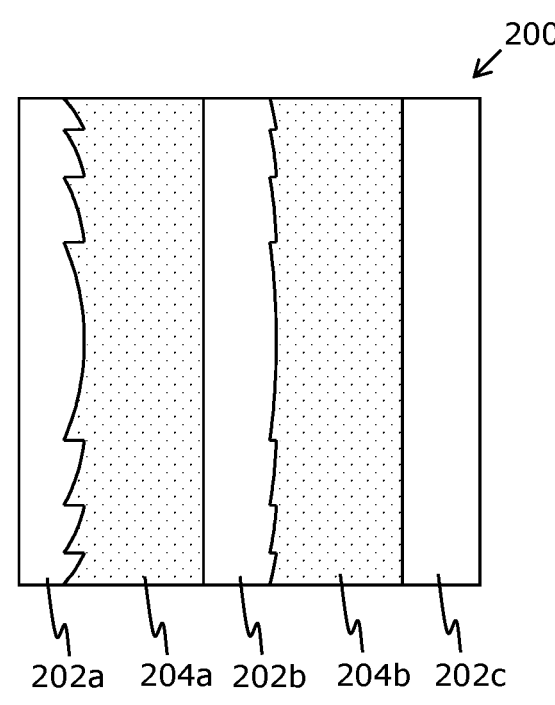

Referring to FIGS. 2A, 2B, and 2C, illustrated are ways in which an optical element 200 can produce different optical powers, in accordance with an embodiment of the present disclosure. The optical element 200 comprises a first substrate 202a, a second substrate 202b, and at least one other substrate (depicted as a third substrate 202c). A cavity 204a is shown to be formed between the first substrate 202a and the second substrate 202b, and another cavity 204b is shown to be formed between the second substrate 202b and the third substrate 202c. With reference to FIGS. 2A, 2B and 2C, the given optical power to be produced depends on a curvature of a surface of the first substrate 202a and the second substrate 202b, and which ones of the cavities 204a and 204b are filled with a gaseous state of the material.

With reference to FIG. 2A, the cavity 204a is filled with a liquid state (as depicted using a zig zag pattern) of the material, and the another cavity 204b is filled with a gaseous state (as depicted using a dotted pattern) of the material. In this case, the given optical power is produced by a curved surface or Fresnel grooves of the second substrate 202b only. With reference to FIG. 2B, the cavity 204a is filled with the gaseous state of the material, and the another cavity 204b is filled with the liquid state of the material. In this case, the given optical power is produced by a curved surface or Fresnel grooves of the first substrate 202a only.

With reference to FIG. 2C, both the cavity 204a and the another cavity 204b are filled with the gaseous state of the material. In this case, the given optical power is produced by the curved surfaces or the Fresnel grooves of both the first substrate 202a and the second substrate 202b.

When both the cavity 204a and the another cavity 204b are filled with the liquid state of the material, the refractive index of the liquid state of the material matches the refractive index of the first substrate 202a and the second substrate 202b. Hence, the optical element 200 emulates a glass slab, and no optical power is produced.

FIGS. 2A, 2B, and 2C are merely examples, which should not unduly limit the scope of the claims herein. It is to be understood that the specific implementations of the optical element 200 are provided as examples and are not to be construed as limiting it to specific arrangements of the substrates or to specific curvatures of the substrates. A person skilled in the art will recognize many variations, alternatives, and modifications of embodiments of the present disclosure.

Figure 3:
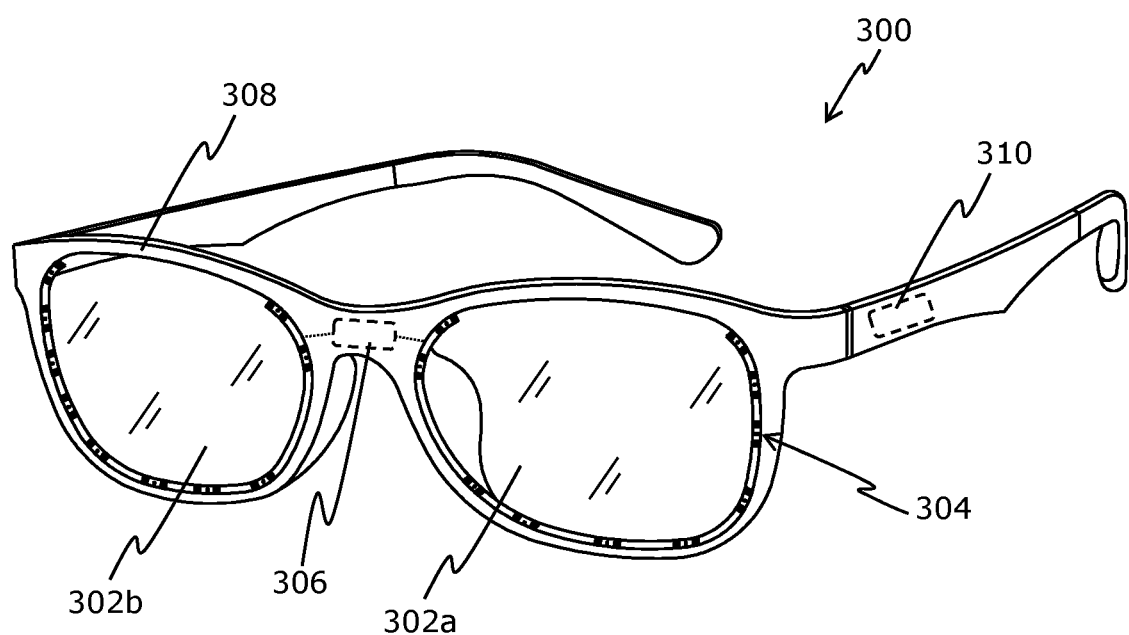
FIG. 3 illustrates a schematic diagram of an optical apparatus, in accordance with an embodiment of the present disclosure.

Referring to FIG. 3, illustrated is a schematic diagram of an optical apparatus 300, in accordance with an embodiment of the present disclosure. As shown, the optical apparatus 300 is implemented as a pair of eyeglasses. The optical apparatus 300 comprises at least one optical element (for example, depicted as optical elements 302a-b). Optionally, the optical apparatus 300 further comprises eye-tracking means 304, a processor 306, a frame 308 for holding the optical elements 302a-b, and at least one input means (depicted as input means 310) mounted on a temple of the frame 308. Optionally, the optical apparatus 300 further comprises a wireless communication interface (not shown) to communicably couple the processor 306 to a computing device (not shown).

FIG. 3 is merely an example, which should not unduly limit the scope of the claims herein. It is to be understood that the specific implementation of the optical apparatus 300 is provided as an example and is not to be construed as limiting it to specific numbers or types of optical elements, eye-tracking means, processors, frames, input means, and wireless communication interfaces. A person skilled in the art will recognize many variations, alternatives, and modifications of embodiments of the present disclosure.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:
1. An optical element comprising:
a first substrate and a second substrate that are optically transparent, wherein a cavity is formed between the first substrate and the second substrate;
a material that is optically transparent, wherein a liquid state of the material has a refractive index that matches a refractive index of at least one of: the first substrate, the second substrate;
a liquid reservoir that is to be employed to hold the liquid state of the material;
a gas reservoir that is to be employed to hold a gaseous state of the material;
means for converting the gaseous state of the material into the liquid state of the material, said means for converting being connected to the gas reservoir and to the liquid reservoir;
at least one fluid channel connecting the cavity to the liquid reservoir and to the gas reservoir; and
means for controlling a supply of the liquid state of the material to the cavity through the at least one fluid channel and for controlling a replacement of the liquid state of the material with the gaseous state of the material in the cavity,
wherein a given optical power is produced by the optical element when the cavity is filled with the gaseous state of the material.
2. The optical element of claim 1, wherein the given optical power to be produced depends on a curvature of a surface of the at least one of: the first substrate, the second substrate, whose refractive index matches with the refractive index of the liquid state of the material.
3. The optical element of claim 1, wherein the at least one of: the first substrate, the second substrate, whose refractive index matches with the refractive index of the liquid state of the material, is implemented as a Fresnel lens having concentric grooves, wherein the concentric grooves face the material.
4. The optical element of claim 1, wherein said means for converting is implemented as a condenser and/or a compressor.
5. The optical element of claim 1, wherein said means for controlling comprises:
a first valve arranged on the at least one fluid channel between the liquid reservoir and the cavity; and
a second valve arranged on the at least one fluid channel between the gas reservoir and the cavity.
6. The optical element of claim 5, wherein said means for controlling further comprises a third valve arranged between the means for converting and the liquid reservoir, wherein the third valve is to be employed to control a condensation and/or a compression of the gaseous state of the material into the liquid state of the material.
7. The optical element of claim 5, wherein said means for controlling comprises a plurality of capillaries that are to be employed to control the supply of the liquid state of the material to the cavity.
8. The optical element of claim 5, wherein the liquid state of the material is supplied from the liquid reservoir to the cavity by:

opening the first valve arranged between the liquid res-
ervoir and the cavity, while closing the second valve
arranged between the gas reservoir and the cavity; and
increasing a pressure at the liquid reservoir.

9. The optical element of claim 5, wherein the liquid state
of the material is replaced with the gaseous state of the
material in the cavity by:

closing the first valve arranged between the liquid reser-
voir and the cavity, while opening the second valve
arranged between the gas reservoir and the cavity; and
reducing a pressure at the gas reservoir.

10. The optical element of claim 1, further comprising:

at least one other substrate, wherein at least one other
cavity is formed between the second substrate and the
at least one other substrate, and wherein the refractive
index of the liquid state of the material matches a
refractive index of at least one of: the second substrate,
the at least one other substrate; and at least one other fluid channel connecting the at least one
other cavity to the liquid reservoir and to the gas
reservoir, wherein said means for controlling is to be employed to
control a supply of the liquid state of the material to the at
least one other cavity through the at least one other fluid
channel and to control a replacement of the liquid state of the
material with the gaseous state of the material in the at least
one other cavity, further wherein the given optical power is produced by the
optical element when at least one of:

the cavity, the at least one other cavity is filled with the
gaseous state of the material.

11. An optical apparatus comprising at least one optical
element of claim 1.

12. The optical apparatus of claim 11, further comprising:

a frame employed to hold the at least one optical element;
and at least one input means, mounted on a temple of the
frame, that is to be used by a user to switch on or switch
off the at least one optical element.

13. The optical apparatus of claim 11, further comprising
a processor and a wireless communication interface that is to
be employed to communicably couple the processor of the
optical apparatus to a computing device, wherein the com-
puting device is to be used by a user for at least one of:

switching on or switching off the at least one optical
element, and inputting the given optical power to be produced.

14. The optical apparatus of claim 11, further comprising
eye-tracking means and a processor configured to:

process eye-tracking data, collected by the eye-tracking
means, to determine gaze directions of a user's eyes;

determine a given optical depth at which the user is
gazing, based on at least one of: the gaze directions of
the user's eyes, depth information of a real-world scene
currently being seen by the user;

determine an optical power prescribed for a given eye of
the user corresponding to the given optical depth at
which the user is gazing, the optical element being
worn in front of the given eye of the user; and determine the given optical power to be produced, based
on the optical power prescribed for the given eye of the
user.

* * * * *